US006969852B2

(12) United States Patent
Yeremin et al.

(10) Patent No.: US 6,969,852 B2
(45) Date of Patent: Nov. 29, 2005

(54) METHOD OF EVALUATING OF A SCANNING ELECTRON MICROSCOPE FOR PRECISE MEASUREMENTS

(75) Inventors: Dmitriy Yeremin, Dobbs Ferry, NY (US); Arkady Nikitin, Yonkers, NY (US)

(73) Assignee: General Phoshonix LLC, Ardsley, NY (US)

( * ) Notice: Subject to any disclaimer, the term of this patent is extended or adjusted under 35 U.S.C. 154(b) by 44 days.

(21) Appl. No.: 10/805,632

(22) Filed: Mar. 22, 2004

(65) Prior Publication Data

US 2005/0205777 A1    Sep. 22, 2005

(51) Int. Cl.[7] ........................... G21K 7/00; H02N 2/02; G01B 5/28
(52) U.S. Cl. ...................... 250/307; 250/306; 250/310; 250/311; 250/491.1; 250/492.1; 250/492.2; 250/492.22
(58) Field of Search ................................ 250/306, 307, 250/310, 311, 491.1, 492.1, 492.2, 492.22, 250/492.3, 201.2, 201.3, 252.1

(56) References Cited

U.S. PATENT DOCUMENTS

| | | | | |
|---|---|---|---|---|
| 3,876,879 A | * | 4/1975 | McAdams et al. | 250/307 |
| 5,684,301 A | * | 11/1997 | Cresswell et al. | 250/306 |
| 5,825,670 A | * | 10/1998 | Chernoff et al. | 702/85 |
| 5,920,067 A | * | 7/1999 | Cresswell et al. | 250/306 |
| 6,197,606 B1 | * | 3/2001 | Polignano et al. | 438/17 |
| 6,570,157 B1 | * | 5/2003 | Singh et al. | 250/311 |
| 6,573,500 B2 | * | 6/2003 | Yeremin et al. | 250/310 |
| 6,608,294 B2 | * | 8/2003 | Nikitin et al. | 250/201.3 |
| 6,664,532 B2 | * | 12/2003 | Yeremin et al. | 250/216 |
| 6,686,587 B2 | * | 2/2004 | Nikitin et al. | 250/237 G |
| 2003/0029997 A1 | * | 2/2003 | Yeremin et al. | 250/307 |
| 2003/0071191 A1 | * | 4/2003 | Nikitin et al. | 250/201.3 |
| 2004/0021075 A1 | * | 2/2004 | Nikitin | 250/307 |
| 2004/0109486 A1 | * | 6/2004 | Kinoshita et al. | 372/45 |

OTHER PUBLICATIONS

Honerkamp, Josef, "Stochastic Dynamical Systems", 1994 VCH Publishers, Inc., Chapter 3.4, pp. 74-86.*

* cited by examiner

Primary Examiner—John R. Lee
Assistant Examiner—Bernard E. Souw
(74) Attorney, Agent, or Firm—Ilya Zborovsky

(57) ABSTRACT

A method evaluating a measuring electron microscope, comprising the steps of setting such modes of operation of a microscope, that will be used for subsequent measurements of sizes and line edge roughness; introducing a test-object which has a known straight edge into a chamber of objects of the microscope; orienting the test object on a stage of the microscope; scanning the test object with an electron beam; obtaining an image of the edge of the test object and saving the image in a digital form; localizing the edge of the test object and saving the image in a digital form; localizing the edge of the test object on the image on each line of scanning; producing storing a set of values of a coordinate X(i) which correspond to a position of the edge of an i-th line of scanning; approximating the sets of values X(i) with a straight line; calculating deviations P(I) of coordinates X(i) from a straight line on each line of scanning; analyzing a set of values of the deviations $\Delta(i)$; calculating an $\Delta_{ave}$ and a maximal deviation $\Delta_{max}$ and if a maximum value of deviation $\Delta_{max}$ exceeds an acceptable tolerance of measurement, making a conclusion whether or not the microscope can be used for measurements and whether or not an adjustment is needed.

6 Claims, 2 Drawing Sheets

| | |
|---|---|
| 1 | Introducing a special test-object into a chamber of the microscope |
| 2 | Orienting of the test object on a stage of the microscope |
| 3 | Scanning the test object with an electron beam |
| 4 | Saving an image of the edge of the test object in a digital form |
| 5 | Localizing the edge of the test object on its SEM image on each line of scanning |
| 6 | Storing a set of values of the coordinate $X(i)$ which correspond to the position of the edge on an i-th line |
| 7 | Approximating the sets of values $X(i)$ or a function $X(i)$ with a straight line |
| 8 | Calculating the deviations $\Delta(i)$ of coordinates $X(i)$ from a straight line on each line of scanning |
| 9 | Analysing of obtained set of values $\Delta(i)$ and calculating an average $\Delta_{ave}$ and a maximal deviation $\Delta_{max}$ |
| 10 | Making the conclusion about the possibility to use the microscope for performing precise measurements |

Figure 2.

METHOD OF EVALUATING OF A SCANNING ELECTRON MICROSCOPE FOR PRECISE MEASUREMENTS

BACKGROUND OF THE INVENTION

The present invention relates to methods of evaluating scanning electron microscopes.

Existing scanning electron microscopes are conventionally evaluated in accordance with the parameters which includes a resolution, a range of magnification, a speed of scanning, a working distance, etc. In recent years the necessity was developed to evaluate scanning microscopes in accordance with their residual scan non-linearity. This is especially actual for measuring scanning microscopes CD SEM. In microscopes of this type, which are provided for precise measurements of small sizes, it is especially important to have perfect systems of scanning, since imperfections of a scan system can lead to unacceptable errors of measurements.

SUMMARY OF THE INVENTION

Accordingly, it is an object of the present invention to provide a method of evaluating of scan system of a scanning electron microscope, which is a further improvement of the inventive methods of this type.

In keeping with these objects and with others which will become apparent herein after, one feature of the present invention resides, briefly stated, in a method of evaluating of a measuring electron microscope, comprising the steps of setting such modes of operation of a microscope, which will be used for subsequent measurements of sizes and line edge roughness; introducing a test-object which has a known straight edge into a chamber of objects of the microscope; orienting the test object on a stage of the microscope so that the edge of the test object is arranged vertically; scanning the test object with an electron beam; obtaining an image of the edge of the test object and saving the image in a digital form; localizing the edge of the test object on the image on each line of scanning; producing and storing a set of values of a coordinate X(i) which correspond to a position of the edge of an i-th line of scanning; approximating the sets of values X(i) with a straight line; calculating deviations $\Delta(i)$ of coordinates X(i) from a straight line on each line of scanning; analyzing a set of values of the deviations $\Delta(i)$; calculating an average $\Delta_{ave}$ and a maximal deviations $\Delta_{max}$; and if a maximum value of deviation $\Delta_{max}$ exceeds an acceptable tolerance of measurement, making a conclusion that the microscope can not be used for measurements and needs an adjustment.

The method of the present invention is based on a research of the inventors, in which during testing of some samples of CD SEM the phenomena of mutual influence of a "fast" line scanning (X-scanning) and "slow" frame scanning (Y-scanning) has been recognized. This phenomena can be the result of several reasons, in particular of an insufficient cross-coupling of the systems of line and frame scans. The influence of the cross-coupling on a SEM image is illustrated herein below in the drawings.

When the method is performed in accordance with the present invention, it eliminates the disadvantages of the prior art.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWING

FIG. 2 shows a flow chart of the actions according to present invention.

DESCRIPTION OF THE PREFERRED EMBODIMENTS

Figure 1:
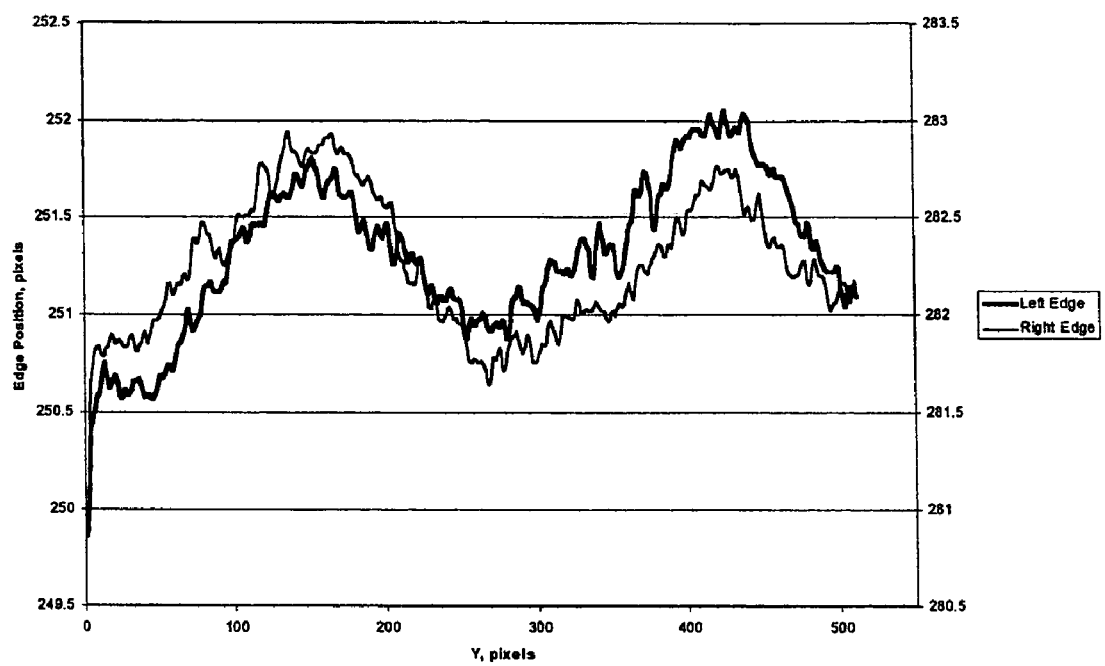
FIG. 1 is a view showing a structure of a left edge and a right edge of one of the strips of a diffraction grating.

FIG. 1 is a view illustrating a principle which is relevant to the present invention. This figure shows structures of a left and a right edge of one of the strips of a diffraction grating which is used as a test object. Symbatic (similar) behavior of these curves clearly shows that their behavior is caused not by individual features of a selected strip, but by specific distortions of an image which characterizes this specific sample of the microscope.

In order to test this concept, comparisons of the shapes of the edges of other strips of the grating, including the strips located at different, arbitrarily selected portions of the grating, were performed. These comparisons show that the shapes edges of the strips has a common symbatic (similar) behavior for all locations. These distortions which are observed on SEM images and characterize a specific measuring microscope can be called a "curvature of a field of SEM image". This parameter has never been used for evaluating, but it is very important for measuring microscopes CD SEM, for precise measurements of sizes, and particular for line edge roughness measurements.

The research conducted by the inventors showed that the scanning microscope of different models and different samples of the same model have different levels of "curvature of the field of SEM image". This curvature also depends on a setting and modes of operation of the microscope. Therefore, evaluation of measuring microscopes in accordance with the parameter "Curvature of the field" can be considered to be a necessary procedure and it must be performed periodically before the process of measurements of sizes and line edge roughness. The present invention allows to perform a calibration of microscope in accordance with this parameter.

In accordance with the present invention, such modes of operation of a microscope are set, which will be later used for subsequent measurements of sizes and line edge roughness. A special test-object which has an a priori known straight edge is introduced into a chamber of objects of the microscope (step 1 in FIG. 2.). The test object is oriented on a stage of the microscope so that an edge of the test object is arranged vertically (step 2 in FIG. 2.).

The test object is scanned with an electron beam (step 3 in FIG. 2.), and an image of the edge of the test object is obtained and saved in a digital form (step 4 in FIG. 2.). The edge of the test object on its SEM image is localized on each line of scanning (step 5 in FIG. 2.) by one of methods, which is known per se in the art and therefore not described here in detail. A set of values of the coordinate X(I) which correspond to the position of the edge on an i-th line is produced and stored (step 6 in FIG. 2.). The sets of values X(i) or a function X(i) is approximated with a straight line (step 7 in FIG. 2.). Then deviations $\Delta(i)$ of coordinates X(i) from a straight line on each line of scanning are calculated (step 8 in FIG. 2.). The thusly obtained set of values Δ(i) is analyzed and an average ave and a maximal deviation $\Delta_{max}$ are calculated (step 9 in FIG. 2.).

After this, a conclusion about the possibility to use or not to use the microscope for performing precise measurements is made (step 10 in FIG. 2.) in accordance with the following criterium:

if a maximum value of deviation $\Delta_{max}$ exceeds an acceptable tolerance of measurement, then the microscope can not be used for measurements and needs an adjustment.

In accordance with the present invention the special test object can be a cleavage surface of a monocrystal composed of an electrically conductive material and having a straight edge. Such crystals can be for example crystals of silicon, of copper, of zinc sulfide ZnS, etc.

The test object introduced into the chamber of objects of the microscope can be formed also as a relief ledge which is formed in a surface layer of a silicon monocrystal by methods of selective chemical etching and having atom-smooth surfaces and straight edges.

In accordance with the present invention the approximation of the set of values X(i) or function X(i) with a straight line can be performed with the use of method of least squares.

In the inventive method, before localization of the edges of the test object on its SEM image on each line, an operation of suppression of noises of the video signal can be performed by a known method.

It will be understood that each of the elements described above, or two or more together, may also find a useful application in other types of methods differing from the types described above.

While the invention has been illustrated and described as embodied in a method of attesting of developments of a scanning electron microscope, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of evaluating a measuring electron microscope, comprising the steps of setting such modes of operation of a microscope, that will be used for subsequent measurements of sizes and line edge roughness; introducing a test-object which has a known straight edge into a chamber of objects of the microscope; orienting the test object on a stage of the microscope; scanning the test object with an electron beam; obtaining an image of the edge of the test object and saving the image in a digital form; localizing the edge of the test object and saving the image in a digital form; localizing the edge of the test object on the image on each line of scanning; producing and storing a set of values of a coordinate X(i) which correspond to a position of the edge of an i-th line of scanning; approximating the sets of values X(i) with a straight line; calculating deviations Δ(i) of coordinates X(i) from a straight line on each line of scanning; analyzing a set of values of the deviations Δ(i); calculating an $\Delta_{ave}$ and a maximal deviation $\Delta_{max}$ and if a maximum value of deviation $\Delta_{max}$ exceeds an acceptable tolerance of measurement, making a conclusion whether or not the microscope can be used for measurements and whether or not an adjustment is needed.

2. A method as defined in claim 1; and further comprising using as a test object a cleavage surface of an electrically conductive monocrystal having a straight edge.

3. A method as defined in claim 2, wherein said monocrystal is a crystal of a material selected from the group consisting of silicon, copper and zinc sulfide ZnS.

4. A method as defined in claim 1; and further comprising using as the test object a relief ledge, which is formed in a surface layer of a monocrystal by methods of selective chemical etching and has atom-smooth surfaces and straight edges.

5. A method as defined in claim 1, wherein said approximating with a straight line includes using a method of least squares.

6. A method as defined in claim 1; and further comprising the steps of suppressing video signal noises before localizing the edges of the test object.

\* \* \* \* \*